United States Patent [19]

Tanaka et al.

[11] Patent Number: 5,068,410

[45] Date of Patent: Nov. 26, 1991

[54] PROCESS FOR PRODUCING HIGHLY PURE 2,6-NAPHTHALENE DICARBOXYLIC ACID

[75] Inventors: Toru Tanaka; Masato Inari, both of Okayama, Japan

[73] Assignee: Mitsubishi Gas Chemical Company, Inc., Tokyo, Japan

[21] Appl. No.: 613,005

[22] Filed: Nov. 15, 1990

[30] Foreign Application Priority Data

Nov. 15, 1989 [JP] Japan .................. 1-294909

[51] Int. Cl.$^5$ .............................................. C07C 57/06
[52] U.S. Cl. ................................................... 562/483
[58] Field of Search ........................................ 562/483

[56] References Cited

U.S. PATENT DOCUMENTS

| | | | |
|---|---|---|---|
| 3,856,855 | 12/1974 | Yamashita et al. | 260/524 R |
| 4,764,638 | 8/1988 | Feld | 562/416 |
| 4,794,195 | 12/1988 | Hayashi et al. | 562/414 |
| 4,886,906 | 12/1989 | Tanaka et al. | 562/416 |

FOREIGN PATENT DOCUMENTS

| | | |
|---|---|---|
| 1299627 | 7/1969 | Fed. Rep. of Germany ...... 562/483 |
| 45-13096 | 5/1970 | Japan . |
| 48-34153 | 5/1973 | Japan . |
| 48-54051 | 7/1973 | Japan . |
| 57-36901 | 8/1982 | Japan . |
| 62-61946 | 3/1987 | Japan . |
| 62-67048 | 3/1987 | Japan . |
| 62-230747 | 10/1987 | Japan . |

*Primary Examiner*—Bruce Gray
*Attorney, Agent, or Firm*—Venable, Baetjer, Howard & Civiletti

[57] ABSTRACT

A process for producing highly pure 2,6-napthalene dicarboxylic acid, characterized by hydrolyzing 2,6-dimethyl naphthalene dicarboxylate more than 99% pure in an aqueous solution by using an aromatic polycarboxylic acid as a catalyst is disclosed.

5 Claims, No Drawings

PROCESS FOR PRODUCING HIGHLY PURE 2,6-NAPHTHALENE DICARBOXYLIC ACID

BACKGROUND OF THE INVENTION

1. Field of the Invention

This invention relates to a process for producing highly pure 2,6-naphthalene dicarboxylic acid which is useful as a raw material for highly functional polymers, such as highly functional polyesters, polyamides and liquid crystal polymers.

2. Prior Art

Prior arts on the production of 2,6-naphthalene dicarboxylic acid (hereinunder referred to as 2,6-NDA) are generally of the following three types.

(1) Processes for producing 2,6-NDA which comprise oxidizing a 2,6-dialkyl naphthalene in the presence of a catalyst comprising a heavy metal and a bromine compound are disclosed in U.S. Pat. No. 3,856,855 and Japanese Patent Application Publication (Kokai) No. 34153/1973.

(2) A process for producing 2,6-NDA which comprises oxidizing 2,6-diisopropyl naphthalene in the presence of a catalyst comprising Co and Mn is disclosed in Japanese Patent Application Publication (Kokai) No. 89445/1985.

(3) Processes for producing 2,6-NDA which comprise oxidizing a 2-alkyl-6-acyl naphthalene in the presence of a catalyst containing Co and Br or Co, Mn and Br or one of these catalysts further containing Fe or Cu are disclosed in Japanese Patent Application Publication (Kokai) Nos. 61946/1987 and 67048/1987 and U.S. Pat. Nos. 4,764,638 and 4,886,906.

The 2,6-NDA obtained by these oxidation methods contains impurities, such as intermediates, such as aldehydes, acyl naphthoic acid, etc.; oxidized polymers; colored materials and the like. Since a highly pure raw material is not necessarily used in the commercial manufacture of 2,6-NDA industrially, the product results in containing impurities contained in the raw material.

When polyesters, polyamides and liquid crystal polymers are produced from the 2,6-NDA containing impurities as mentioned above, films or fibers obtained from these polymers have poor physical properties such as poor thermal resistance, mechanical strength and dimension stability, and quality in these films or fibers are likely to be lowered due to the discoloration. Therefore, the production of 2,6-NDA which is more than 99% pure has been demanded.

Prior arts on the purification of the 2,6-NDA obtained by the above-mentioned methods are as follows:

(1) a process which comprises dissolving the crude 2,6-NDA in an aqueous alkaline solution, concentrating the solution to deposit the dialkali salt of 2,6-NDA, dissolving the dialkali salt in water, bubbling a carbon dioxide gas into the solution to deposit the monoalkali salt of 2,6-NDA, dissolving the separated monoalkali salt in water and disproportionating the monoalkali salt by heating it, thereby depositing 2,6-NDA [refer to Japanese Patent Publication (Kokoku) No. 13096/1970].

(2) a process which comprises dissolving the crude 2,6-NDA in an aqueous alkaline solution, carrying out catalytic hydrogenation of the 2,6-NDA in the presence of palladium, platinum, ruthenium or the like as a catalyst at a temperature of not more than 220° C., bubbling a carbon dioxide gas into the solution to deposit the monoalkali salt of 2,6-NDA, dissolving the separated monoalkali salt in water and disproportionating the monoalkali salt by heating it, thereby depositing 2,6-NDA [refer to Japanese Patent Publication (Kokoku) No. 36901/1982].

(3) a process which comprises dissolving the crude 2,6-NDA in an aqueous alkaline solution, heating the solution at 100°-250° C., decoloring the 2,6-NDA solution with activated carbon, concentrating the solution to deposit the dialkali salt of 2,6-NDA, dissolving the dialkali salt in water and adding an acid to the solution to deposit the object product [refer to Japanese Patent Application Publication (Kokai) No. 54051/1973].

(4) a process which comprises adding the crude 2,6-NDA to an aqueous solution containing an alkali and a neutral salt containing the same cation constituting the alkali compound, agitating the solution to deposit the dialkali salt of 2,6-NDA, dissolving the separated dialkali salt in a 1–3 wt % aqueous solution of sodium chloride, treating the solution with activated carbon and depositing the object product with carbon dioxide or sulfurous acid gas [refer to U.S. Pat. No. 4,794,195].

(5) a process which comprises dissolving the crude 2,6-NDA in an organic solvent, such as N,N-dimethyl acetamide, N,N-dimethyl formamide, dimethyl sulfoxide or the like at 80°-189° C., treating the solution with activated carbon and cooling the solution to −15° to 40° C. to recrystallize the object product [refer to Japanese Patent Application Publication (Kokai) No. 230747/1987].

However, in processes (1) and (2), it is difficult to control the proportion of the components constituting crystal and the amount of monoalkali salt of 2,6-NDA due to the delicate equilibrium between (a) an monoalkali salt of 2,6-NDA and a dialkali salt of 2,6-NDA and (b) an acid in the step for depositing the monoalkali salt by adjusting the pH. In addition, since the monoalkali salt of 2,6-NDA is water soluble, the monoalkali salt is eluted in washing with water, the mother liquor which has adhered to the crystal after filtration. This results in a lowering of the yield of 2,6-NDA.

In processes (3) and (4), a fine particle size crystal having a size as small as 1 μm is deposited when depositing the object product with an acid. As a result, it becomes difficult to filter or rinse the cake.

In process (5), a large amount of an expensive organic solvent such as N,N-dimethyl acetamide, N,N-dimethyl formamide, or dimethyl sulfoxide must be used. In addition, it is difficult to treat such an organic solvent, due to the odor and toxicity of these solvent. Therefore, it is difficult to carry out process (5) on a commercial scale.

It is impossible to purify 2,6-NDA by distillation, because the compound has a melting point of not less than 300° C.

As mentioned above, it is difficult to obtain highly pure 2,6-NDA by purifying the crude 2,6-NDA.

Therefore, the present inventors have attempted the production of highly pure 2,6-NDA by esterifying crude 2,6-NDA, followed by hydrolyzing the resulting dimethyl ester of 2,6-NDA (hereinunder referred to as 2,6-NDM).

2,6-NDM can be purified by distillation. In addition, it is easy to recrystallize 2,6-NDM and treat 2,6-NDM with a solid adsorbent, since 2,6-NDM is easily dissolved in an organic solvent. 2,6-NDM itself is used as a raw material for polyester. Therefore, the purification of 2,6-NDM has been established.

Hydrolysis or saponification is used for producing 2,6-NDA from 2,6-NDM. However, when 2,6-NDM is saponified, the dialkali salt of 2,6-NDA is formed. The above-mentioned problem occurs in case of deposit the dialkali salt of 2,6-NDA with an acid. The hydrolyzing operation proceeds slowly in the absence of any catalyst. When 2,6-NDM is hydrolyzed in the presence of a generally used mineral acid such as sulfuric acid as a catalyst, the reaction proceeds rapidly. However, the resulting crystal is too fine for filtering or washing.

SUMMARY OF THE INVENTION

The present inventors have conducted further research to obtain a highly pure 2,6-NDA. As a result, when an aromatic poly-carboxylic acid is used as a catalyst instead of a mineral acid, it is found that the reactivity is high, and that the resulting 2,6-NDA crystal is large enough to be filtered or rinsed. The present invention is based on this finding.

This invention relates to a process for producing highly pure 2,6-naphthalene dicarboxylic acid, characterized by hydrolyzing 2,6-dimethyl naphthalene dicarboxylate more than 99% pure in an aqueous solution by using an aromatic poly-carboxylic acid or an anhydride thereof as a catalyst.

DETAILED DESCRIPTION OF THE INVENTION 2,6-NDM which is used as a raw material in the present invention can be produced by oxidizing a 2,6-dialkyl naphthalene or a 2-alkyl-6-acyl naphthalene as mentioned above, thereby forming 2,6-NDA, followed by esterifying the resulting 2,6-NDA in the presence of sulfuric acid (catalyst) in a methanol solvent at 100°–200° C. 2,6-NDM can be purified by distillation, both of distillation and treatment with a solid adsorbent; or recrystallization. Purity of the purified 2,6-NDM was measured by chemical analysis such as gas chromatography or high speed liquid chromatography.

The amount of water used in the solution in the present invention may be 2–15 times by weight of the amount of 2,6-NDM, and preferably 5–10 times by weight of the amount of 2,6-NDM. If the amount of water is less than 2 times by weight, the concentration of methanol formed by the hydrolysis becomes high, and as a result, high reactivity cannot be achieved due to the poor equilibrium. If the amount of water is more than 15 times by weight, reactivity does not change. This is not economical.

Examples of the aromatic poly-carboxylic acids include phthalic acid, trimellitic acid, pyromellitic acid and the like. The anhydrides thereof can be used. The acid can be used alone or as a mixture. The concentration of the aromatic poly-carboxylic acid may be in the range of 2–20% by weight and preferably 2.5–15% by weight. If the concentration of the aromatic poly-carboxylic acid is less than 2% by weight, the reaction speed is slow. If the concentration of the carboxylic acid is more than 20% by weight, this is not economical, due to the lack of change in the reactivity.

The reaction temperature may be in the range of 200°–230° C., and preferably 210°–220° C. If the reaction temperature is less than 200° C., the action of the catalyst is lowered, and as a result, the reactivity is lowered. If the reaction temperature is more than 230° C., corrosive action of the carboxylic acid shall be stronger, and as a result, the carboxylic acid corrosion shall be occurred on the surface of the vessel material.

The reaction pressure may be such a pressure that the reaction system is maintained to a liquid phase. Therefore, the reaction pressure depends on the reaction temperature.

The present reaction may be carried out in an inert gas not containing oxygen. If oxygen is present in the gaseous phase in the reaction vessel, the 2,6-NDM is likely to be discolored, and decomposition of the aromatic poly-carboxylic acid is promoted.

When the present reaction is carried out at the above-mentioned temperature range in an inert gas, the aromatic poly-carboxylic acid is stable, and it is observed that decomposition of the carboxylic acid after the reaction hardly occurs.

After the reaction is completed, the reaction mixture is cooled to about 80° C. to crystallize the 2,6-NDA. The 2,6-NDA is separated from the mother liquor by filtration, and is rinsed with hot water to remove the mother liquor and deposited catalyst from the crystal, thereby obtaining highly pure 2,6-NDA in a high yield.

According to the present invention, highly pure 2,6-NDA can be obtained without using a large amount of alkali, which remains as an inorganic ion in the object product, or any expensive solvent.

In addition, since 2,6-NDA is hardly dissolved in water, 2,6-NDA is not eluted in the separated mother liquor and a rinsing solution as the case of alkaline or organic solvent.

The 2,6-NDA crystal particles which are obtained by hydrolyzing 2,6-NDM in the presence of an aromatic poly-carboxylic acid as a catalyst have a large particle size. Therefore, it is easy to wash the separated cake and there is few or no crystal particles which pass through the filter during filtration, and as a result, all or most of the crystal particles purified can be recovered.

Therefore, the present invention has the following advantages:

(1) The recovery rate of 2,6-NDA is strikingly high;
(2) The operation of the present invention is easy;
(3) Any alkali or any expensive solvent are not used; and
(4) It is unnecessary to treat the exhaust formed by the present invention.

Consequently, the present invention is excellent from an industrial point of view.

This invention is further explained by way of the following non-limiting examples. All percentages are on a weight basis, unless specified otherwise.

EXAMPLE 1

Into a 100-ml zirconium autoclave were charged 60 g of water, 10 g (14.2% solution in an solvent) of pyromellitic acid and 10 g of 2,6-NDM. The gaseous phase in the autoclave was purged with nitrogen.

The 2,6-NDM used was prepared by the process which comprises:

a step of oxidizing 2-methyl-6-butylnaphthalene to form 2,6-NDA;

a step of esterifying the 2,6-NDA with a 1% sulfuric acid solution in methanol to form crude 2,6-NDM 99% pure; and a step of distillation of the crude 2,6-NDM to form white 2,6-NDM.

The autoclave was placed in an aluminum block heater, and the hydrolysis was carried out at 220° C. for 2 hours while agitating the mixture by shaking the autoclave. After the reaction was completed, the mixture was cooled to 80° C. and then the autoclave was opened. Thereafter, the reaction mixture was filtered and the product was rinsed and dried. The resulting crystal particles were white. When the particle size distribution of the crystal particles was measured, the average particle size thereof was 60 μm and the uniformity index thereof was 2.2. A color-difference meter showed an L-value of 97.0, a-value of −0.3 and b-value of 3.7. Gas chromatograph analysis did not reveal the presence of any impurity. The acid value thereof 519 mg KOH/g (theoretical acid value of 2,6-NDA is 519 mg KOH/g). These analytic data show that the resulting 2,6-NDA was pure. The product (9.39 g) was obtained, and the yield was 99%.

EXAMPLE 2

The procedure of Example 1 was repeated except that pyromellitic acid (5 g) was used, and hydrolysis was carried out at 210° C. for 4 hours. The results are shown in Table 1.

EXAMPLES 3-5

The procedures of Example 1 were repeated except that trimellitic acid (Examples 3-4) and phthalic acid (Example 5) were used instead of pyromellitic acid. The results are shown in Table 1.

CONTROL RUNS 1-3

The procedures of Example 1 were repeated except that sulfuric acid was used instead of pyromellitic acid.

CONTROL RUN 4

The procedure of Example 1 was repeated except that the hydrolysis was carried in the absence of any acidic catalyst. The acid value of the resulting 2,6-NDA was 140 mg KOH/g, and its yield was 40%.

CONTROL RUN 5

The procedure of Example 3 was repeated except that the gaseous phase in the autoclave was not purged with nitrogen. The resulting reaction liquid was brown, and the separated 2,6-NDA crystal was light red. Color-difference meter showed an L-value of 95.2, a-value of 0.1 and b-value of 6.0. This example means that oxygen in the gaseous phase in the autoclave gives a bad effect to the color of the resulting product.

What is claimed is:

1. A process for producing highly pure 2,6-naphthalene dicarboxylic acid, characterized by hydrolyzing 2,6-dimethyl naphthalene dicarboxylate more than 99% pure in an aqueous solution by using an aromatic poly-carboxylic acid or an anhydride thereof as a catalyst.

2. The process of claim 1 wherein the concentration of the aromatic poly-carboxylic acid in an aqueous solution is in the range of 0.2–20% by weight.

3. The process of claim 1 wherein the hydrolysis is carried out in an inert atmosphere.

4. The process of claim 1 wherein the hydrolysis is carried out at 200°–230° C.

5. The process of claim 1 wherein the hydrolysis is carried out at such a pressure that the reaction system is kept in a liquid phase.

TABLE 1

|  | Example | | | | | Control Run | | |
|---|---|---|---|---|---|---|---|---|
|  | 1 | 2 | 3 | 4 | 5 | 1 | 2 | 3 |
| Catalyst amount (g) | pyromellitic acid | pyromellitic acid | trimellitic acid | trimellitic acid | phthalic acid | sulfuric acid | sulfuric acid | sulfuric acid |
|  | 10 | 5 | 10 | 1.5 | 10 | 1 | 1 | 1 |
| Reaction temperature (°C.) | 220 | 210 | 220 | 220 | 220 | 220 | 210 | 200 |
| Reaction time (hr.) | 2 | 4 | 2 | 3 | 3 | 2 | 2 | 4 |
| Acid value (mg KOH/g) | 519 | 518 | 519 | 518 | 519. | 519 | 518 | 518 |
| Color  L | 97.0 | 97.0 | 97.1 | 97.0 | 97.3 | 97.0 | 96.4 | 97.3 |
| a | −0.3 | −0.1 | −0.3 | −0.5 | −0.5 | −0.3 | −0.3 | −0.3 |
| b | 3.7 | 3.0 | 3.2 | 3.3 | 3.3 | 3.7 | 2.6 | 3.0 |
| Average particle size (μm) | 60 | 57 | 59 | 51 | 67 | 25 | 27 | 27 |
| Uniformity index | 2.2 | 1.9 | 1.8 | 1.5 | 1.6 | 1.2 | 1.3 | 1.2 |
| Yield (%) | 99 | 98 | 98 | 97 | 99 | 75 | 76 | 73 |